United States Patent [19]

Catot et al.

[11] Patent Number: 5,363,702

[45] Date of Patent: Nov. 15, 1994

[54] DEVICE FOR INSPECTING THE RIM OF A RAILWAY WHEEL

[75] Inventors: Bernard Catot, Leffrinckoucke; Vaerio Del Fabbro, Marly; Guy Stevenot, Dunkerque, all of France

[73] Assignee: Valdunes, Puteaux, France

[21] Appl. No.: 75,878

[22] Filed: Jun. 14, 1993

[30] Foreign Application Priority Data

Jun. 18, 1992 [FR] France ............... 92 07433

[51] Int. Cl.$^5$ ............................................. G01H 1/00
[52] U.S. Cl. ................................ 73/598; 73/593; 73/81
[58] Field of Search .............. 73/598, 593, 597, 624, 73/649, 658, 661, 81

[56] References Cited

U.S. PATENT DOCUMENTS

| | | | |
|---|---|---|---|
| 3,596,503 | 8/1971 | Gay | 73/625 |
| 3,978,712 | 9/1976 | Cowan | 73/628 X |
| 4,164,141 | 8/1979 | Sandor | 73/81 |
| 4,679,358 | 7/1987 | Siederadzki | 51/165.72 |
| 4,719,793 | 1/1988 | Pozo | 73/81 |

FOREIGN PATENT DOCUMENTS 2105845  3/1983  United Kingdom ............... 73/649

*Primary Examiner*—Thomas P. Noland
*Assistant Examiner*—Christine K. Oda
*Attorney, Agent, or Firm*—Oblon, Spivak, McClelland, Maier & Neustadt

[57] ABSTRACT

The device includes a stand, a rail for supporting the wheel fixed to a horizontal part of the stand, longitudinal guide members fixed to a vertical part of the stand and extending in a direction parallel to the rail, slideways fixed to the horizontal part of the stand and extending in a direction parallel to the rail, and a carriage movable along the slideways. The carriage carries a grinding device and a hardness measuring device. Means permit applying a force on the hardness measuring device. An ultrasonic inspection device carried by the carriage may also be provided.

7 Claims, 2 Drawing Sheets

DEVICE FOR INSPECTING THE RIM OF A RAILWAY WHEEL

TITLE OF THE INVENTION

1. Field of the Invention

The present invention relates to a ball-test inspection of the hardness of the rim of a railway wheel and to the ultrasonic inspection of the residual stresses in the rim.

2. Discussion of the Background

Railway wheels obtained by forging and heat treatment must be inspected. The hardness and the residual stresses of the rims must be in particular inspected. For this purpose, lengthy manual operations are required for the preparation of the surface and the inspection.

SUMMARY OF THE INVENTION

An object of the present invention is to facilitate these inspection operations by providing automatic means for achieving them.

The invention therefore provides a device for inspecting the rim of a railway wheel, characterized in that it comprises:

a stand having a horizontal part in the shape of a quadrilateral and at least one vertical part parallel to one of the edges of the horizontal part, a rail for supporting the wheel fixed to the horizontal part of the stand and extending in a direction parallel to the vertical part of the stand, longitudinal guide members for the wheel fixed to the vertical part of the stand and extending in a direction parallel to the rail, a longitudinal member parallel to the longitudinal wheel guiding members and mounted to be movable in a direction perpendicular to the longitudinal guide members and parallel to the horizontal part of the stand, means for shifting the movable longitudinal member for applying it against the wheel, slideways fixed to the horizontal part of the stand and extending in a direction parallel to the rail, a carriage mounted to be movable in translation on the slideways, means for shifting the carriage, a grinding device carried by the carriage and mounted on the carriage to be movable in a direction perpendicular to the slideways, means for shifting the grinding device, a ball-test device carried by the carriage for measuring hardness, a device for applying a predetermined force against the ball-test device for measuring hardness.

The ball-test device comprises a ball-test head slidably mounted in a sleeve, said head having a dome or receiving end, and a linear sensor for sensing the displacement of the ball-test head.

The device for applying a predetermined force on the ball-test device may comprise a lever pivotally mounted on the stand, a screw jack provided with a motor, carried by the lever and applicable against the dome or receiving end of the ball-test device, a counterweight adapted to bear against the arm of the lever, a jack for raising the counterweight, a jack for releasing the counterweight, and a support for the counterweight raising and releasing jacks.

Preferably, the device further comprises an ultrasonic inspection device mounted to be movable in translation on the carriage in a direction perpendicular to the slideways, means for shifting the ultrasonic inspection device between an operative position in contact with the rim of the wheel and a withdrawn position, a position detector of a mechanical type mounted on the carriage to be movable in a direction perpendicular to the slideways, and means for shifting the detector between a withdrawn position and a position in which it bears against the rim of the wheel.

The ultrasonic inspection device comprises a head for transmitting and receiving ultrasonic shear waves mounted to be rotatable about a horizontal axis parallel to the axis of displacement of the ultrasonic inspection device, means for rotating the transmitting and receiving head and means for distributing coupling fluid.

Preferably, the means for shifting in translation the carriage, the grinding device, the ultrasonic inspection device and the mechanical position detector are pneumatic jacks.

The device according to the invention comprises electropneumatic and electronic control means.

Lastly, the rail has in its upper part a V-shaped notch for stopping the wheel in the measuring and inspection position.

BRIEF DESCRIPTION OF THE DRAWINGS

The invention which permits carrying out automatic inspections of railway wheels will now be described with reference to the accompanying drawings, in which.

DESCRIPTION OF THE PREFERRED EMBODIMENTS

Figure 1:
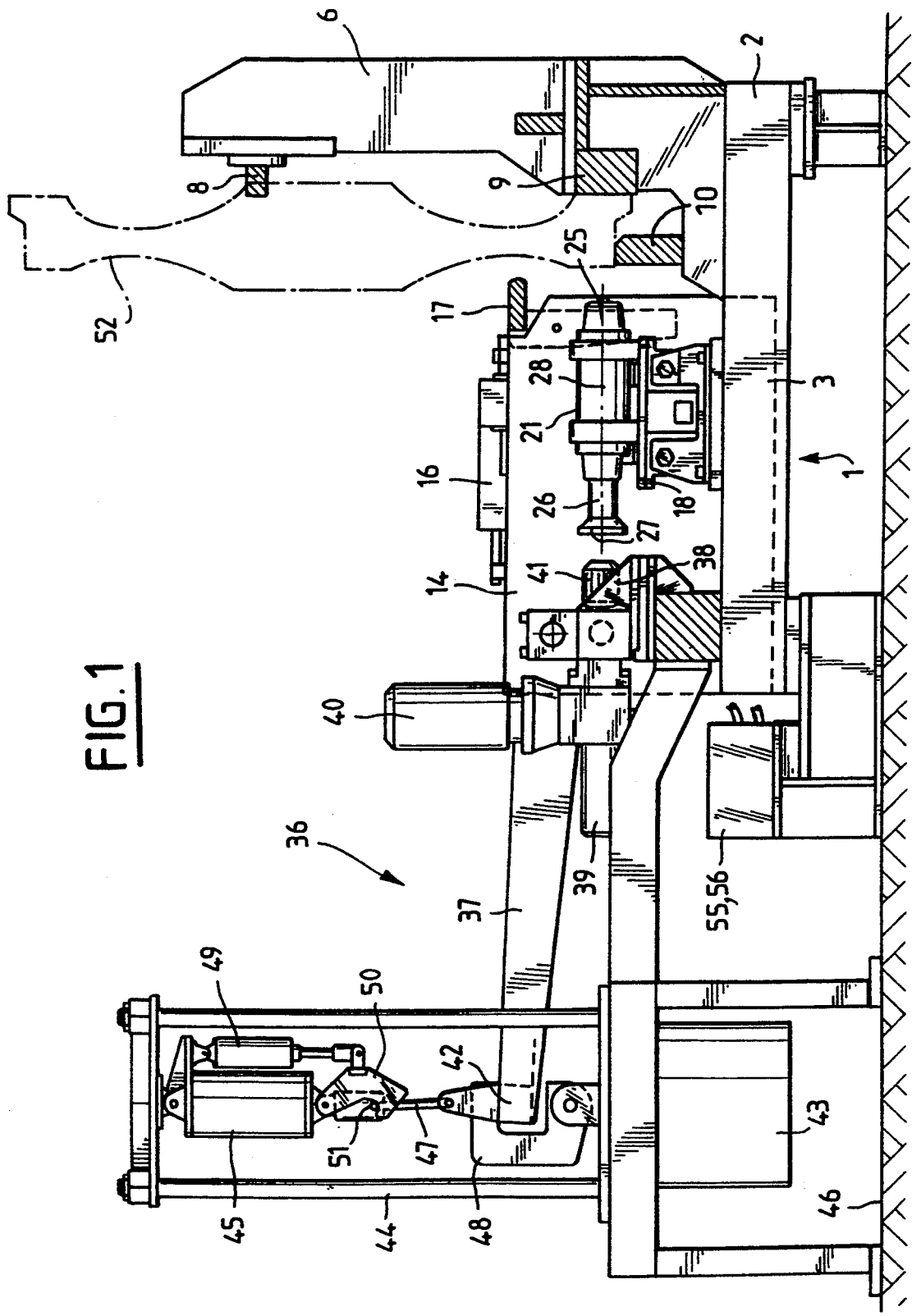
FIG. 1 is an elevational view of the device according to the invention the stand of which shown in a vertical section plane.
Figure 2:
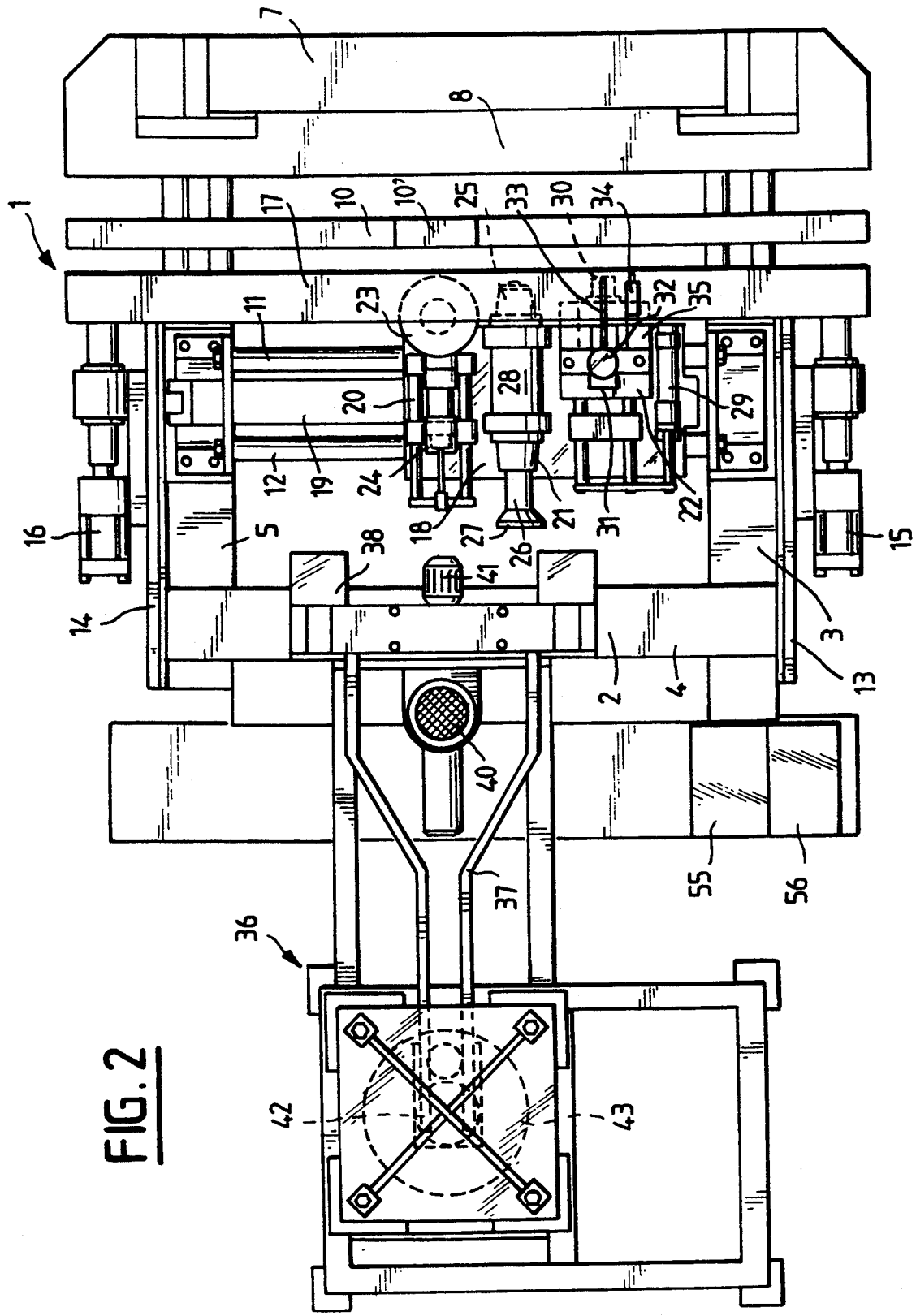
FIG. 2 is a top plan view.

The device comprises a stand designated by the general reference character 1 and consisting of a horizontal frame 2 formed by beams 3, 4, 5, and vertical posts 6, 7 located adjacent one of the ends of the beams 3 and 5 so that, when viewed in side elevation, the stand is L-shaped.

The posts 6 and 7 carry horizontal longitudinal members 8, 9. The horizontal frame carries a rail 10 provided with a V-shaped notch 10' in its upper part roughly on the axis of the device.

The horizontal frame also carries vertical side walls 13, 14 perpendicular to the rail 10 and on which are fixed jacks 15, 16 the rods of which carry a movable longitudinal member 17 parallel to the rail 10 and to the fixed longitudinal members 8, 9. The jacks permit shifting the movable longitudinal member 17, while maintaining it parallel to itself, toward the plane containing the fixed longitudinal members 8 and 9.

Slideways 11, 12, fixed to the horizontal part of the stand 1 and extending in a direction parallel to the rail 10, carry a carriage 18 which is movable in translation by means of a pneumatic jack 19.

Mounted on the carriage side by side and one after the other in the transverse direction are:

a grinding device 20, a ball-test device 21 for measuring hardness, an ultrasonic inspection device 22 for inspecting residual stresses.

The grinding device 20 has a rotating grinding wheel 23 mounted to be movable on the carriage 18 in a direction perpendicular to the slideways 11, 12. The grinding wheel 23 may be shifted by means of a pneumatic jack 24.

The ball-test device 21 comprises a ball-test head 25 mounted on a stem 26 which carries at one end a dome or receiving end 27 and is slidable in a sleeve 28.

This device also includes means (not shown) for measuring the displacement of the ball-test head.

The ultrasonic device 22 for inspecting residual stresses is mounted to be movable in a direction perpendicular to the slideways 11, 12 and can be shifted by means of a pneumatic jack 29. It comprises a head 30 transmitting and receiving ultrasonic shear waves and mounted to be rotatable about a horizontal axis parallel to the axis of displacement of the ultrasonic inspection device, and a jack 31 for shifting the head 30 in rotation.

The ultrasonic inspection device 22 also comprises means for feeding coupling fluid constituted by a metering pump 32 and a pipe 33 which opens out in proximity to the transmitting and receiving head.

A position detector 34 of a mechanical type is mounted on the support 35 of the ultrasonic inspection device 22, so that it is displaceable in a direction perpendicular to the slideways 11, 12 by means of the jack 29.

A device 36 permits applying a predetermined force on the ball-test head 25 through the stem 26 and the dome 27.

This device 26 comprises a lever 37 which is pivotally mounted at one end 38 on the transverse beam 4 of the stand 1 and carries in the part thereof in proximity to the end 38 a screw jack 39 having a motor 40 and a head 47 which is cooperative with the dome 27, and at the other end 42 of the lever remote from the pivotal connection, a counterweight 43.

A support 44 resting on the ground 46 carries a first jack 45 the rod of which is connected to a hook 48 from which the counterweight 43 is suspended.

The support 44 carries a second jack 49 capable of actuating a hook 50 which is pivoted to the body of the jack 45 and is capable of hooking onto a pin 51 fixed to the end of the rod of the jack 45.

The assembly 36 is so disposed that the axis of the screw jack 39 is approximately in alignment with the V-shaped notch 10' of the rail 70.

The inspection of a wheel 52 is carried out in the following manner:

The wheel is brought onto the rail 10 and maintained in position in the V-shaped notch 10', by means of the jacks 15 and 16 and by applying the longitudinal member 17 against the wheel in such manner as to clamp the wheel between the longitudinal members 8, 9 on one hand and the longitudinal member 17 on the other hand.

By means of the jack 19, the grinding wheel 23 is brought in front of the rim of the wheel in the region of the V-shaped notch, then, by means of the jack 24, the grinding wheel is applied against the rim and the rim is locally ground by feeding the grinding wheel 23 in a reciprocating motion by means of the jack 19, and then the grinding wheel is withdrawn.

By means of the jack 19, the position detector 34 is brought in front of the ground zone and then, by means of the jack 29, the detector 34 is applied against the rim of the wheel and the position of the detector is recorded, which permits measuring the thickness of the rim. The detector 34 is then withdrawn.

By means of the jack 19, the transmitting and receiving head 30 is brought in front of the ground zone and the head 30 is applied against the rim of the wheel 52 by means of the jack 29; coupling liquid is supplied by means of the metering pump 32 and a first measurement of the time of propagation of the ultrasonic waves in the rim is effected; then the transmitting and receiving head 30 is made to rotate through a quarter of a turn by means of the jack 31 and a second measurement of the time of propagation of the ultrasonic waves is effected, then, by means of the jack 29, the transmitting and receiving head is withdrawn.

The measurement of the thickness of the rim and the measurements of the time of propagation of the ultrasonic waves in the rim permit determining the residual stresses in the latter.

When the residual stresses have been measured, the ball-test head 25 is brought by means of the jack 19 in front of the ground zone. The head 41 of the screw jack 39, the dome 27, the stem 26, the ball-test head 25 and the ground zone of the rim are then in alignment and the head 41 of the screw jack 39 is applied by means of the motor 40 against the dome 27 so as to apply the ball-test head 25 against the rim of the wheel with a force on the order of 200 kg. Then the hook 50 is retracted by means of the jack 49, which releases the counterweight 43 which, by bearing against the lever 37, comes to apply the head 41 against the dome 27 and thereby apply the ball-test head 25 against the rim of the wheel with a force of 3000 kg. By means of the displacement detecting means, the displacement in the axial direction of the ball-test head 25 is measured between the position thereof when it is applied against the rim with a force of 200 kg and the position thereof when it is applied against the rim with a force of 3000 kg. Thus displacement permits calculating the hardness of the rim from the measured penetration of the ball.

After the hardness has been measured, the counterweight 43 is raised by means of the jack 45 and this engages the pin 51 on the hook 50 so that the counterweight is held in an upper position.

All of the jacks and the measuring means are connected to electropneumatic control devices 55 and to electronic control means 56 so that all the movements can be effected automatically.

It will be understood that the device just described may be constructed with equivalent means, in particular for guiding and shifting the various movable elements.

What is claimed is:

1. Device for inspecting a rim of a railway wheel by measuring under a predetermined force the hardness of said rim, wherein said device comprises:
  a stand comprising a horizontal part in the shape of a quadrilateral and at least one vertical part which is parallel to an edge of said horizontal part,
  a rail for supporting said wheel, said rail being fixed to said horizontal part of said stand and extending in a direction parallel to said at least one vertical part of said stand,
  a plurality of longitudinal guide members for guiding said wheel, said longitudinal guide members being fixed to said at least one vertical part of said stand and extending in a direction parallel to said rail,
  a movable longitudinal member positioned parallel to said longitudinal guide members,
  a shifting mechanism connected to said movable longitudinal member for moving said longitudinal member in a direction perpendicular to said longitudinal guide members and parallel to said horizontal part of said stand and for contacting said longitudinal member against said wheel, a plurality of slideways fixed to said horizontal part of said stand and extending in a direction parallel to said rail, a carriage mounted on said slideways for moving along the slideways, a mechanism for shifting said carriage on said slideways, a grinding device mounted on said carriage and connected to said shifting mechanism for moving the grinding device on said carriage in a direction perpendicular to said slideways, a ball-test device carried by said carriage for measuring hardness of said rim under the predetermined force, and a device mounted on said stand for applying the predetermined force on said ball-test device.

2. The device according to claim 1, wherein said ball-test device comprises a cylindrical sleeve, a cylindrical stem coaxially mounted with play within said sleeve, a ball-test head mounted at one end of said stem, said stem having a receiving end remote from said ball-test head, and a linear sensor for sensing displacement of said ball-test head.

3. The device according to claim 1, wherein said device for applying a predetermined force on said ball-test device comprises:

a lever pivotally mounted on said stand, a screw jack mounted on said stand and having a motor, carried by said lever and including a moving part arranged for contacting and pushing said receiving end of said ball-test device, a support part connected to said stand, a counterweight suspended to said support part, said support part bearing against said lever, a first jack connected to said counterweight for raising the counterweight, a second jack connected to said counterweight for releasing said counterweight, a fixed support for supporting said counterweight, said jack for raising and said second jack for releasing said counterweight.

4. The device according to claim 1, which comprises:

an ultrasonic inspection device mounted on said carriage for moving in translation along an axis perpendicular to said slideways, a mechanism for shifting said ultrasonic inspection device between an operative position in which said inspection device is in contact with said rim of said wheel and a withdrawn position, a mechanical position detector mounted on said carriage for moving on said carriage in a direction perpendicular to said slideways, and a mechanism for shifting said detector between a withdrawn position and a position in which said detector contacts said rim of said wheel.

5. The device according to claim 4, wherein said ultrasonic inspection device comprises a head for transmitting and receiving ultrasonic shear waves mounted on said carriage for rotation about a horizontal axis parallel to a displacement direction of said ultrasonic inspection device, a rotating actuation mechanism for rotatably shifting said transmitting and receiving head, and a mechanism for distributing coupling fluid connected to said ultrasonic inspection device.

6. The device according to claim 4, wherein said mechanism for shifting said carriage, said grinding device, said ultrasonic inspection device, and said mechanical position detector each comprises a pneumatic jack.

7. The device according to claim 1, wherein said rail has in an upper part thereof a V-shaped notch for stopping said wheel at a position for measuring and inspection said wheel.

* * * * *

UNITED STATES PATENT AND TRADEMARK OFFICE
CERTIFICATE OF CORRECTION

PATENT NO. : 5,363,702
DATED : November 15, 1994
INVENTOR(S) : Bernard CATOT, et al.

It is certified that error appears in the above-indentified patent and that said Letters Patent is hereby corrected as shown below:

On the title page, Item [75], the second inventor's name is spelled incorrectly. It should read:

--Valerio Del Fabbro--

Signed and Sealed this

Fourteenth Day of February, 1995

Attest:

BRUCE LEHMAN

*Attesting Officer*   *Commissioner of Patents and Trademarks*